US005795755A

United States Patent [19]

Lemelson

[11] Patent Number: 5,795,755
[45] Date of Patent: Aug. 18, 1998

[54] METHOD OF IMPLANTING LIVING CELLS BY LASER PORATION AT SELECTED SITES

[76] Inventor: Jerome H. Lemelson, Suite 286, Unit 802, 930 Tahoe Blvd., Incline Village, Nev. 89451-9436

[21] Appl. No.: 605,716

[22] Filed: Feb. 22, 1996

Related U.S. Application Data

[63] Continuation-in-part of Ser. No. 270,741, Jul. 5, 1994, abandoned.
[51] Int. Cl.$^6$ .................... C12N 13/00; C12N 15/63; C12M 3/04
[52] U.S. Cl. ................. 435/173.5; 435/172.3; 435/285.2
[58] Field of Search .................... 435/172.1, 172.2, 435/172.3, 173.1, 173.4, 173.5, 173.6, 285.1, 285.2

[56] References Cited

U.S. PATENT DOCUMENTS

| | | | |
|---|---|---|---|
| 4,849,355 | 7/1989 | Wong | 435/173.6 |
| 4,927,254 | 5/1990 | Kino et al. | 359/235 |
| 4,970,154 | 11/1990 | Chang | 435/172.2 |
| 5,013,660 | 5/1991 | Kasuya et al. | 435/172.3 |
| 5,065,008 | 11/1991 | Hakamata et al. | 250/216 |
| 5,296,703 | 3/1994 | Tsien | 250/235 |

OTHER PUBLICATIONS

Ariel, M. D., Irving M., "Progress in Clinical Cancer", vol. 3, pp. 205–220 Crane & Stratton, Inc.: 1967.
Vozelp et al Experientia. vol. 28(9): pp. 1098–1099 "Argon Laser", 1972.
Goldman, M.D., Leon, Prog. Clin. Cancer, vol. 3: pp. 205–220 "Laser Treatment of Cancer", 1967.
Goldman, M.D., Leon, Prog. Clin. Cancer, "The Laser in Dermatology", 1980, pp. 329–331.
Johnston, J.H. and D.M. Jensen, W. Mautner, J. Elashoff, "YAG Laser Treatment of Experimental Bleeding Canine Gastric Ulcers", Gastroenterology, vol. 79 pp. 1252–1261 1980.
Kavetsky, R.E. and N.F. Gamaleja, "Lasers as Tools for Oncology", Variety of Lasers (unnumbered pages) 1973.
Schwartzberg, Daniel and Faiq J. Al-Bazzaz, John Cassel, Albert Andrews Jr. and Immacula Cantave, "Multiple Granular Cell Tumors of the Bronchi", American Review of Respiratory Disease, vol. 120: pp. 193–196 1979.
Silverstein, F.E. and r.L Protell, C. Gulacsik, D. C. Auth, M. Deltenre, M. Dennis, J. Piercey and C. Rubin, "Endoscopic Laser Treatment", Gastroenterology, vol. 74: pp. 232–239 1978.

*Primary Examiner*—George C. Elliott
*Assistant Examiner*—Terry A. McKelvey
*Attorney, Agent, or Firm*—Niro, Scavone, Haller & Niro

[57] ABSTRACT

A method and apparatus for operating on living cells in order to transfer material to the interior of selectively targeted cells is disclosed. The operation may take place in a reaction chamber in which a group of cells are disposed, only some of which are desired to receive material which serves to transform or otherwise affect the cells. In one embodiment, certain of the cells in the reaction chamber are targeted by computerized image analysis of images of the cells as generated by confocal microscopy. The targeted cells are then transfected with genetic material using a computer controlled laser beam. The laser beam creates pores in the membranes of the targeted cells through which genetic material also present within the reaction chamber may pass. An electric field may also be employed to facilitate pore formation.

10 Claims, 1 Drawing Sheet

METHOD OF IMPLANTING LIVING CELLS BY LASER PORATION AT SELECTED SITES

This application is a continuation-in-part of application Ser. No. 08/270,741 filed on Jul. 5, 1994, abandoned.

BACKGROUND AND SUMMARY OF THE INVENTION

The present invention relates to apparatus and methods for transferring material into living cells to transform or otherwise affect the cells. Such methods are commonly used in genetic engineering applications to transfer genes to cells where they then produce a protein product. Other applications of such methods include the delivery of agents such as antibodies or drugs to intracellular targets. Most methods used today for such purposes, however, are relatively non-specific and result in the transfer of material to a collection of cells in relatively non-specific fashion. For example, methods for transferring genes to cells such as calcium phosphate coprecipitation, lipofection, electroporation, and particle bombardment involve the foreign DNA being transferred at random to certain ones of a collection of cells. Heretofore, the only way to transfer DNA, or any other material, to specifically identified cells was by means of microinjection techniques. Microinjection, however, is very slow and tedious, and it accordingly cannot be used to transfer genes to a large number of cells.

The present invention is defined by a system and method for reacting on biological matter, in vitro or in vivo, with controlled radiant energy, such as electromagnetic, and/or sonic energy to: (a) investigate the effects of such radiation on the matter, (b) selectively change the structure of such matter to attain a new structure thereof, (c) treat such matter to enhance its growth or structure, (d) permit or control a reaction involving such matter and one or more additional chemical and/or biological agents added thereto, (e) genetically alter such biological matter, (f) selectively destroy such matter in the presence of a select chemical or biological agent, or a combination of such processes. In a preferred form, a computer is employed to control and analyze sensing signals generated by one or more sensors employed to sense variations in the biological matter during and/or after the application of such electromagnetic, and/or sonic energy to such matter. The electromagnetic, and/or ultrasonic or subsonic radiation may be variably generated as to duration, frequency, intensity, and time(s) of application during a reaction cycle or analysis interval under the control of a computer which is programmed to control the reaction and is operable to analyze sensing signals and control the reaction in accordance therewith using artificial intelligence techniques such as expert systems and neural networks.

In one form of the invention, a plurality of different forms of radiation are sequentially and/or simultaneously controllably applied to the reaction materials under computer control and the results are sensed by one or more sensors such as by one or more photoelectric detectors, x-ray or NMR scanners, biosensors or the like, or any combination thereof. In another particular form, one or more select amounts such as simple elements, groups of biological elements, or batches thereof, are observed before, while, or after being subjected to one or more forms of radiant energy directed therat as a field or as one or more beams. The radiant energy may cause the biological elements to fluoresce and may also be supplemented with or replaced by direct and/or alternating current passed through the matter under observation, which current is computer controlled in duration, voltage, amperage, frequency, etc. The results of such externally applied stimuli are sensed and the sensing signals are computer analyzed to generate control codes which are applied to (a) intelligibly indicate changes in the structure of the biological matter and (b) effect further control of the energy employed to affect the matter.

In another particular form, first matter such as DNA is applied to second matter such as one or more living cells to genetically alter or affect the latter. One of the above-described forms of energy is used to effect the reaction such as to cause the DNA to enter and genetically alter the cells wherein the radiant energy is operable to control such reaction and/or to induce insertion of the DNA into such cell. In other forms, the controlled radiant energy operates to effect and/or accelerate the insertion of the DNA or other matter into living cells or otherwise affect the biological reaction. In one particular embodiment, genetic material is transferred to select living cells disposed within a reaction chamber where they may be examined with a confocal microscope. The confocal microscope generates image signals, such as by a photodetector array which converts the light intensity of each point in an image field into an electrical signal, which image signals are then analyzed by a computer. The computer thus identifies and classifies individual cells residing within the reaction chamber and computes a location coordinate for each identified cell. A laser beam controlled by the computer as to direction and intensity is then used to create transient pores within the cell membrane of select cells. The pores thus created allow genetic material such as RNA or DNA (or other substances such as proteins) to enter the cell. In order to further enhance gene transfer into the cell, an electric field is impressed across the reaction chamber which field serves to effect or to facilitate the creation of pores by the laser beam as well as stabilize them.

In still another specific embodiment of the invention, the location of specific pieces of exogenous material such as DNA fragments to be added to a living cell is sensed using one or more sensors such as confocal microscopes, photoelectric detectors, x-ray or NMR scanners, biosensors or the like, or any combination thereof. The identity of such pieces of exogenous material is determined by computer analysis of the images of such material. That information is combined with computer analysis of the location and surface configuration of specific living cells, to yield a digital map showing the relative location of the surfaces of such cells and the exogenous material which is desired to be added to the cells. Information from the digital map is then used by the computer to identify specific locations on the surfaces of target cells which are close to specific pieces of exogenous material which is desired to be added to the cells. A laser beam controlled by the computer as to direction and intensity is then used to create transient pores through the surface of the cell membrane at the specific locations close to the exogenous material which is to be incorporated into the cells. The pores created by this process allow the specifically-targeted pieces of exogenous material to enter the cells at the specific, targeted locations on the cell membranes. In this fashion exogenous material such as DNA, RNA, monoclonal antibodies, proteins, etc. can be implanted into chosen cells at particular, chosen locations from a liquid medium which may contain many forms of exogenous material, some of which it may not be desired to incorporate into the cells. Thus, in this embodiment it is possible not only to target specific cells but also to implant exogenous material into the cells at specific locations on their surfaces. It is also possible to implant only certain, chosen fragments of exogenous material from the liquid medium into the cells. while excluding other fragments of exogenous material whose implantation is not desired.

It is therefore a primary object of the present invention to provide a method and apparatus for using radiant energy to selectively transfer material to living cells.

It is a further object of the invention to provide a method and apparatus for transfecting individually targeted cells with genetic material.

Other objects, features, and advantages of the invention will become evident in light of the following detailed description considered in conjunction with the referenced drawings of a preferred exemplary embodiment according to the present invention.

DETAILED DESCRIPTION OF A PARTICULAR EMBODIMENT

Figure 1:
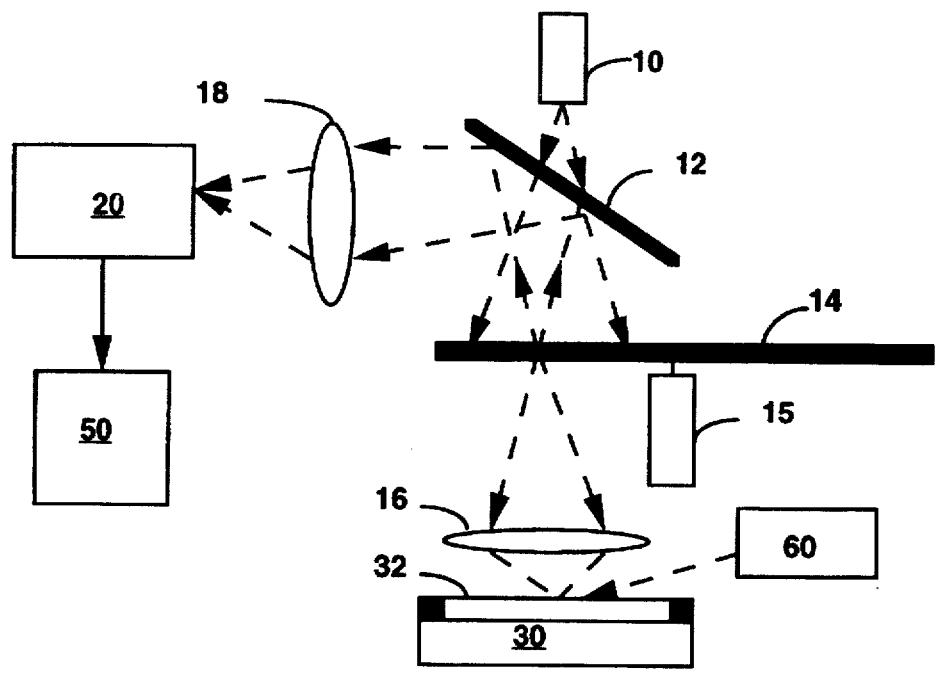
FIG. 1 is a schematic of an apparatus in accordance with the invention showing the components of the confocal microscope.

In the specific embodiment of the invention to be described below, a material such as foreign DNA is transferred into specifically identified cells residing within a reaction chamber. Such identified cells may be, for example, cancerous cells or cells of a specific tissue type in which a desired change will be effected by the transferred genetic material. In order to accomplish this, a tissue specimen, or other collection of cells, is disposed in a liquid medium contained within the reaction chamber which also contains the foreign DNA. In order to target specific cells within the reaction chamber, an image of the specimen is produced using scanning confocal microscopy. The image is then analyzed by computer to identify the specific cells within the chamber which are to receive the DNA. Once the location coordinates of such cells are determined, a laser beam is directed at the cells in order to create pores in the membranes thereof. The pores then allow the passage of the foreign DNA into the interior of the selected cells.

In another embodiment of the invention, specific areas of the cell membrane may be targeted based upon sectioned images of specific cells created by confocal microscopy. This enables optimum choice of insertion points, taking account of internal cell structure. For example, DNA fragments can be inserted close to the structures with which bonding is desired.

1. Generation of confocal microscopic image

A basic confocal microscope is an instrument in which illuminating light from a laser or other source is passed through a transmitting aperture so as to create a diffraction-limited point source, and then focused by a microscopic objective lens at a point within the specimen being examined. Light reflected from the region so illuminated is then focused by the objective lens on a receiving aperture which then transmits the light to a photodetector such as a photomultiplier tube. The receiving aperture acts as a spatial filter to remove light other than that reflected from the point at which the transmitted light is focused, so that only light from the maximally illuminated point is received by the photodetector. An image of the specimen is obtained by moving the specimen relative to the illuminating light beam or deflecting the light beam in x and y (ie., horizontal) directions. Light from each successive point in the specimen thus scanned is then received by the photodetector which feeds a signal representing the intensity of the reflected light to a computer for construction of a composite two-dimensional image. Due to the spatial filtering by the receiving aperture, not only is light by the photodetector restricted to that reflected from specific points in the x-y plane, but the instrument also has a very short depth of focus along the optical or vertical axis. This means that the composite two-dimensional images are of specific layers of the specimen which is what allows whole, non-sectioned cells to be imaged by confocal microscopy. By combining the images of a plurality of such layers, a three-dimensional image of the specimen may be obtained.

Although a confocal microscope such as that described above may be used in the present invention for certain applications, the time required to construct an image of the specimen is somewhat slow. In order to identify and direct radiation in real-time at select cells within the reaction chamber which are suspended within a liquid, or are otherwise mobile, high-speed scanning techniques must be employed. One such high-speed scanning technique involves the use of a plurality of transmitting apertures to simultaneously illuminate a plurality of points in the specimen. Light reflected therefrom is then focused on a plurality of corresponding receiving apertures by the objective lens, which light from each such aperture is then focused by an imaging lens on a specific points of a vidicon or an array of photodetectors. By moving the transmitting and receiving apertures, the specimen is rapidly scanned so that a complete image is obtained. One particular arrangement of moving apertures which may be used for confocal microscopy is a so-called Nipkow disk. (See Xiao et al., *SPIE Scanning Imaging Technology*, 809, 107, (1987)).

FIG. 1 shows in schematic form a confocal microscopy arrangement for high-speed scanning of a specimen in accordance with the present invention. Light from a laser 10 is passed through a beam splitter 12 and thence to a Nipkow disk 14 having a plurality of apertures arranged in interleaved spirals. From each aperture of the disk 14 the light travels to a microscopic objective lens 16 which focuses the light through transparent window 32 at a specific point within the reaction chamber 30. The light reflected from each point so illuminated within the reaction chamber 30 is then focused by lens 16 on the same apertures of disk 14 used to transmit the illumination beam. The spatially filtered light from disk 14 is then transmitted via beam splitter 12 to an imaging lens 18 which focuses light from each illuminated point within the reaction chamber on a vidicon or array of solid-state photodetectors 20. A motor 15 is employed to rotate the disk 14 so as move the apertures and scan an entire focal plane within the reaction chamber 30. A complete image of one layer of the specimen within chamber 30 is thus produced upon photodetector array 20. From the photodetector array 20, the resulting pixel intensity values are then transmitted to a computer 50 for analysis as described below. The computer 50 controls the components of the confocal microscopy apparatus so as to obtain images of as many select planes within the reaction chamber 30 as are needed in order to identify the cells within the chamber. Once target cells are identified, the computer 50 controls the operation of a power laser 60 to direct a laser beam at such cells and create pores in the membranes thereof.

In certain embodiments, the laser 10 may comprise one or more lasers which emit light at a wavelength which causes specific cell components to fluoresce. Such fluorescent cell components may be naturally occuring or artificially added to the cells. The resulting fluorescently emitted light is then detected to form an image as described above.

2. Image analysis

As described above, the images produced by the confocal microscope are converted into electronically manipulable form by a vidicon or an array of solid-state photosensors such as, for example, photodiodes, charge injection devices (CIDs), or charge coupled devices (CCDs). In the case of a vidicon, the resulting analog video signal is digitized and fed to the computer 50 which then constructs an array of pixel intensity values wherein each pixel corresponds to a point within reaction chamber 30 with a set of specified location coordinates. The analog outputs of a photosensor array, on the other hand, are digitized directly into an array of digital pixel intensity values which may be fed to the computer 50 either serially or in parallel. The resulting array of pixel intensity values can then be analyzed in the manner described below in order to identify specific features within the image and, when converted to analog gray scale values, may be used to drive a CRT or the like and thus provide a visual display of the image.

The digitized image signals generated as described above are analyzed by the computer 50 in order to search for specific cells into which it is desired to transfer DNA. The image data is first converted into codes representing features extracted from the image which allow the system to both identify and classify individual cells in the sample. In order to extract specific image features, the image data signals are subjected to a segmentation process which groups the pixels of the image into distinct entities representing identifiable structures. Such segmentation may be accomplished by methods well-known to those of skill in the computer vision art such as: (1) edge-based approaches where intensity discontinuities are detected, and the pixels are then clustered into regions bounded by the detected edges, (2) textural segmentation approaches where the image is partitioned into non-overlapping regions based on textural homogeneity of groups of pixels which may involve, for example, either region growing by sequentially adding similar pixels to a local starting point, or region splitting where the entire image is sequentially divided into smaller regions on the basis of pixel intensity dissimilarity, or (3) matching approaches utilizing standard images of different cell types and subcellular structures which are used as templates for matching with analogous structures in the input image. A system in accordance with the present invention may make use of any or all of those methods as well as other pattern recognition methods such as neural networks.

After the segmentation process, the system then processes the image data into information which is useable by the system in classifying cells into different types so as to identify, for example, cancerous cells or cells of a specific tissue. Such information will typically include the size and shape of the segmented regions within a specific cell as well as the spatial distribution of a pattern of intensities over a particular region (ie., its texture). The resulting extracted features from the input image are next interpreted by a rule-based artificial intelligence program of a type sometimes referred to as a production system or an expert system. Such a program may comprise (1) a knowledge database having a set of rules or productions which allow the generation of image classification information on the basis of identified features, (2) a fact database which includes features extracted from the image, and (3) a control program or inference engine operable for determining the applicability of the rules in the context of the current database, the selection of appropriate rules, and operating on the fact database by means of the selected rules.

The knowledge database contains the logic used by the system in evaluating the significance of each feature in the fact database. Each rule of the knowledge database is typically in the form of an implication or IF-THEN statement. Each such rule thus has a premise and a conclusion where the premise may consist of any number of clauses representing factual statements or conclusions which are combined disjunctively or conjunctively. When the premise is satisfied, the rule is "fired," and the rule's conclusion is taken by the system to be true. That conclusion may then be used by the system in activating other rules and so on. The rules thus represent the relationships between image features and conclusions about what is contained in the image based on a knowledge of histology. The ultimate conclusions contained in the rules are typically explicit statements reflecting an identification of the cell type. Using what is referred to as forward-chaining, database facts and/or conclusions from applicable rules are linked to the premises of other rules until one or more ultimate conclusions are reached. The system may also perform backward-chaining of rules in order to test hypotheses about specific features in the image such as a cell's classification. The hypotheses to be tested are generated by the system as the product of rules. In backward-chaining, conclusions are linked to premises containing factual statements, the latter being compared with the fact database. The chaining process is continued until premises are identified which, according to the fact database, establish the conclusion as true.

The method of data analysis described above is that of a rule-based artificial intelligence system. Alternative embodiments of the present invention may make use of fuzzy logic rules operating on data coded according to its degree of membership in fuzzy sets. Such fuzzy logic rules may be used both in feature extraction and as part of the knowledge database used to generate conclusions.

3. Gene transfer

Figure 2:
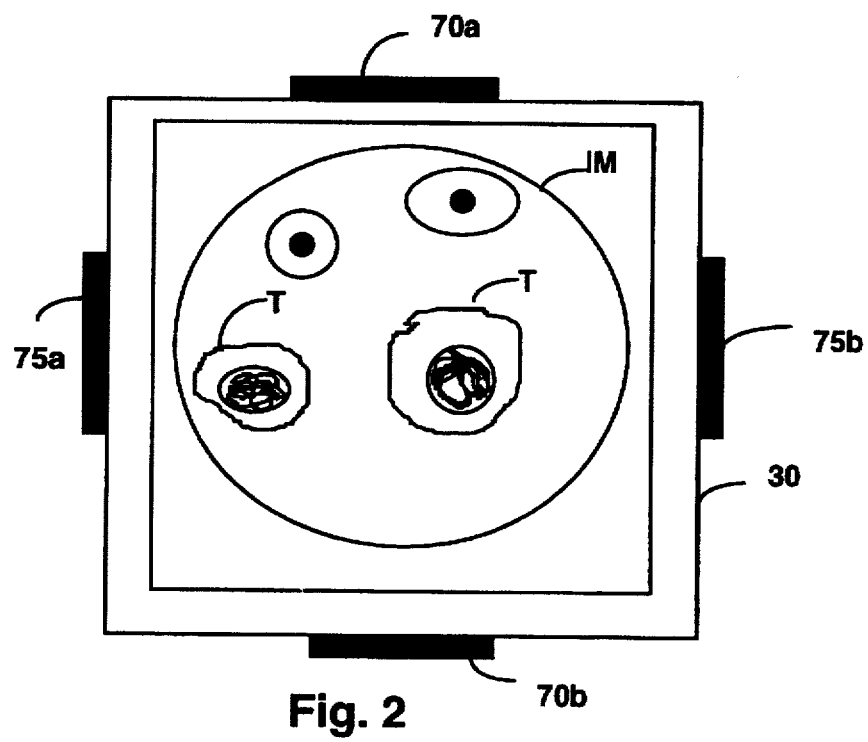
FIG. 2 shows schematically a view of the reaction chamber as imaged by the confocal microscope.

Once target cells are identified within an image, the location coordinates of each such cell within the reaction chamber are computed. The location coordinates of a targeted cell are used to direct a pulsed laser beam thereat at an intensity which then creates a pore in the cell membrane through which foreign DNA may pass into the interior of the cell. Repetitive pulsing of the laser beam may be used to create a plurality of such pores. FIG. 2 depicts a view of the reaction chamber 30 showing a magnified image IM as imaged by the confocal microscope. The chamber 30 contains a collection of different cells such as may be found in a patient's blood or other tissue sample. For simplicity's sake, only a few such cells are shown with the cells identified as target cells designated T. A power laser 60, such as an excimer laser, directs a laser beam into the reaction chamber 30, either from above through transparent window 32 as shown or from a side of the reaction chamber through a separate transparent port, which beam may be deflected under the control of the computer 50 so as to impinge on a selected cell at its computed location coordinates. A plurality of such power lasers may be employed in order to facilitate complete coverage of the reaction chamber volume.

In order to further enhance the intracellular delivery of DNA into the targeted cells, an electric field may be imposed across the reaction chamber in conjunction with the laser pulses. Such an electric field polarizes the membranes of the cells so as to facilitate pore formation. In the conventional DNA transfection technique known as electroporation, high amplitude electric field pulses (ie., 5 kV/cm or greater) are used by themselves to create pores in cell membranes for the intracellular delivery of DNA. (See Neumann et al., *EMBO*

J. 1. 841 (1982)). According to currently accepted theories, hydrophobic pores are created in the lipid matrix of cell membranes by local thermal fluctuations when an electric field of sufficient amplitude is applied thereto. These hydrophobic pores are converted into hydrophilic pores through which polar molecules such as DNA fragments may pass by the pressure of water dielectrically drawn into the pore where the electric field intensity is maximal. After the pulse is terminated, the pores reseal. Conventional electroporation efficiently transfers DNA into cells, but does so in a non-specific fashion as noted above. In accordance with the present invention, a low amplitude electric field pulse (eg., .5 kV/cm or less) is applied to the reaction chamber 50 in conjunction with laser pulses directed at targeted cells. Such low amplitude electric field pulses are insufficient by themselves to cause the formation of hydrophobic pores within the cell membranes. Instead, thermal energy received at the cell membrane from the laser beam creates the hydrophobic pore which is then converted into a hydrophilic pore by the low intensity electric field pulse. In this manner, the electrically induced hydrophilic pores are restricted to targeted cells.

For such electrically induced pore formation to occur, the electric field should optimally be oriented in a direction perpendicular to the plane of the hydrophobic pore initially created by the laser beam. FIG. 2 shows two sets of electrodes 70a–b and 75a–b which, under the control of the computer 50, produce electric field pulses across the reaction chamber 30 of a specified amplitude and duration. By superposition of electric field pulses, an electric field may be produced which is directed along any arbitrary axis of the horizontal plane. A third set of electrodes (not shown) oriented along the vertical axis enables the electric field to be directed along any arbitrary axis. Thus the computer 50 may cause an electric field pulse to be generated which matches any arbitrarily directed laser beam.

Other embodiments of the invention involve the simultaneous and/or sequential application of two or more forms of energy (microwave, RF, laser, ultrasonic, spark, or electric) to the reaction matter to either prepare the cells or receipt of matter such as DNA or to effect the transfer. A computer predeterminately varies the power, voltage, amperage, frequency, or other characteristic of the input energies. A computer may also be employed to control a cell manipulator and/or an energy field to move and position the cells individually and/or in clusters with respect to the laser of other form of energy generator. Such computer control of the manipulator or energy field may be used in conjunction with computer control of the deflection of pore forming energy directed at the cells in accordance with feedback signals indicative of their position in order to effect the desired results.

In another embodiment, a laser beam is used to excite fluorescent components of cells, which fluorescent radiation is then analyzed by a spectral computer. Such spectral analysis may be employed alone or in combination with image analysis to detect cancerous or precancanaerous cells.

In still another embodiment, confocal microscopic techniques described above are used not only to identify the location of specific cells, but also to provide images of the surfaces of such cells as well as section images of their internal structure. Segmentation techniques described above are then applied to the sectioned images to identify optimum points on the cell surface for insertion of exogenous material such as DNA fragments, based upon the internal structure of the cell. This allows more-precise targeting of the laser used for creating pore In a variation on this embodiment, confocal microscopic techniques described above are also used to identify specific types of exogenous material, and the locations of specific fragments of such material. That information is combined by the computer with the images of specific cell surfaces to identify target locations on cell surfaces that are close to desired fragments of exogenous material. Laser radiation can then be used to create transient pores at specific locations on cell walls that are near desired fragments of exogenous material, which enables insertion of only desired fragments of exogenous material into specific cells, while excluding undesired materials that also may be present in the liquid solution.

Although the invention has been described in conjunction with the foregoing specific embodiment, many alternatives, variations, and modifications will be apparent to those of ordinary skill in the art. Those alternatives, variations, and modifications are intended to fall within the scope of the following appended claims.

What is claimed is:

1. A method of transferring exogenous material into living cells comprising the steps of:

disposing a specimen of said living cells within a reaction chamber together with the exogenous material;

sensing a plurality of images of the surfaces of said living cells and sections of said living cells, and generating cell sensing signals from said plurality of images;

transmitting said cell sensing signals to a computer and operating said computer to identify desired cells in the specimen, identify desired specific locations on the surfaces of said desired cells, and determine location coordinates within the reaction chamber for the desired specific locations; and under control of the computer, generating and directing at least one source of laser light energy at the location coordinates, whereby said laser light energy creates transient pores in the desired specific locations through which the exogenous material passes.

2. The method of claim 1, wherein the exogenous material comprises fragments of foreign DNA.

3. The method of claim 1, wherein the exogenous material comprises monoclonal antibodies directed against intracellular targets within the desired cells.

4. The method of claim 1, wherein said plurality of images are sensed in the spectrum of radiation fluorescently emitted from said living cells.

5. The method of claim 1, further comprising applying an electric field to the specimen at a low intensity just sufficient to facilitate the creation of said transient pores.

6. The method of claim 1, wherein said plurality of images are sensed by generating confocal microscopic images of the specimen.

7. The method of claim 6, wherein said confocal microscopic images are generated by scanning the living cells with light passing through a plurality of moving apertures.

8. An apparatus for transferring exogenous material into living cells comprising:

a chamber defining a volume of space sufficient to retain and hold a specimen of said living cells and said exogenous material within its boundaries and having a means for accessing the inside of said chamber and at least one transparent window;

a confocal microscope for sensing a plurality of images of the surfaces of said living cells and sections of said living cells;

a photo detector array for generating cell sensing signals from said plurality of images;

a computer for analyzing said cell sensing signals in order to identify desired cells in the specimen and for determining location coordinates within the reaction chamber for the desired cells;

a pair of electrodes for applying an electric field to the specimen under control of said computer in order to facilitate formation of pores in the membranes of the desired cells; and a radiant energy generating device under control of said computer for directing radiant energy at the desired cells in order to create the pores in the membranes thereof through which said material may pass.

9. The apparatus of claim 8, wherein said confocal microscope contains a plurality of moving apertures through which illuminating and reflected light passes in order to scan the specimen.

10. A method of selectively transferring desired exogenous material into living cells comprising the steps of:

disposing a specimen of said living cells within a reaction chamber together with the exogenous material;

sensing a plurality of images of the surfaces of said living cells and sections of said living cells, and generating cell sensing signals and exogenous material sensing signals from said plurality of images;

transmitting said cell sensing signals and said material sensing signals to a computer and operating said computer to identify desired cells in the specimen, identify desired specific locations on the surfaces of the desired cells, identify specific locations of desired exogenous material, and determine location coordinates within the reaction chamber for poration sites, which poration sites are said desired specific locations on the surfaces of the desired cells which are sufficiently close to said specific locations of desired exogenous material to permit the selective passage of said desired exogenous material into the desired cells; and under control of the computer, generating and directing at least one source of laser light energy at the location coordinates, whereby said laser light energy creates transient pores in the poration sites through which the desired exogenous material selectively passes.

\* \* \* \* \*